United States Patent [19]

Voss

[11] 4,341,865

[45] Jul. 27, 1982

[54] DETERMINATION OF THYROXINE BINDING GLOBULIN

[75] Inventor: Houston F. Voss, Libertyville, Ill.

[73] Assignee: Abbott Laboratories, North Chicago, Ill.

[21] Appl. No.: 170,361

[22] Filed: Jul. 21, 1980

[51] Int. Cl.$^3$ .............................................. G01N 33/54
[52] U.S. Cl. ........................................ 435/7; 435/188;
435/810; 424/8; 424/12; 23/230 B
[58] Field of Search ............... 424/1, 8, 12; 23/230 B;
435/7, 177, 188, 184, 810

[56] References Cited

U.S. PATENT DOCUMENTS

| | | | |
|---|---|---|---|
| 3,935,074 | 1/1976 | Rubenstein et al. | 435/7 |
| 4,043,872 | 8/1977 | Blakemore et al. | 435/7 |
| 4,120,754 | 10/1978 | Barendz | 435/20 |
| 4,134,792 | 1/1979 | Boguslaski et al. | 435/7 |
| 4,168,207 | 9/1979 | Yoshida et al. | 435/7 |
| 4,230,797 | 10/1980 | Boguslaski et al. | 435/7 |
| 4,233,401 | 11/1980 | Yoshida et al. | 435/7 |
| 4,238,471 | 12/1980 | Reese et al. | 23/230 B |
| 4,273,866 | 6/1981 | Voss et al. | 435/7 |

FOREIGN PATENT DOCUMENTS 864856 9/1978 Belgium.
2754086 6/1978 Fed. Rep. of Germany.

OTHER PUBLICATIONS

Aaron et al., "The Stereo Chemistry of Asymmetric Phosphorous Compounds II. Stereospecificity in the Irreversible Inactivation of Cholinesterases by the Enantiomorphs of an Organophosphorous Inhibitor", J. Am. Soc. Chem., vol. 80, (1958), pp. 456–458.
Aaron et al., "The Stereochemistry of Asymmetric Phosphorous Compounds III. The Resolution of a Series of O-Alkyl Alkylphosphonothioic Acids, "J. Am. Soc. Chem., vol. 82, (1960), pp. 596–598.
Boter et al., "Organophosphorous Compounds Part V", Rec. Trav. Chim., vol. 86, (1967), pp. 399–404.
Pilz, "Cholinesterases", Meth. Enzym. Anal., vol. 2, 2nd ed., Bergmeyen ed., (1974) pp. 831–835.
Levine "Determination in Blood with Automated Analysers", Meth. Enzym. Anal., vol. 2, 2nd ed., Bergmeyer ed., (1974) pp. 851–855.
Aldridge et al., Enzyme Inhibitors as Substrates, North-Holland Publishing Co., Amsterdam, (1972), pp. 5–6.
Kaptein et al., "Free Thyroxine Estimates in Nonthyroidal Illness: Comparison of Eight Methods", J. Clin. Endocrin. Metab., vol. 52, No. 6 (1981), pp. 1073–1077.

Primary Examiner—Thomas G. Wiseman
Attorney, Agent, or Firm—John J. McDonnell

[57] ABSTRACT

This invention encompasses a method for measuring unsaturated thyroxine binding globulin in serum comprising intermixing with the serum:
 (i) thyroxine irreversible enzyme inhibitor conjugate which binds to the unsaturated thyroxine binding globulin thereby inactivating the irreversible enzyme inhibitor portion of the conjugate;
 (ii) an enzyme which is irreversibly inhibited by the thyroxine irreversible enzyme inhibitor conjugate unbound by the thyroxine binding globulin; and
 (iii) a substrate for the enzyme; and monitoring the enzyme substrate reaction.

4 Claims, No Drawings

DETERMINATION OF THYROXINE BINDING GLOBULIN

BACKGROUND OF THE INVENTION

Free thyroxine is the generally accepted marker for the initial assessment of possible thyroid dysfunction: J. Clin. Invest., 45:133, 1966. Since approximately 0.05% of the total circulating thyroxine is physiologically active (i.e., free thyroxine), it is apparent that measurement of total thyroxine concentration only is not a completely satisfactory marker. Free thyroxine is however difficult to measure directly: Berger, S., and Quinn, J. L., "Fundamentals of Clinical Chemistry", Tietz, N. W., Ed; W. B. Saunders, Co.: Philadelphia, 1976, Chapter 14 and Robbins, J., "Thyroid Hormone Metabolism", Proceedings of an International Symposium at Glasgow, Harlem and Orr, Ed., 1975, Chapter 1. The remaining circulating thyroxine is bound to protein, primarily thyroxine binding globulin (TBG): Robbins, J., and Rall, J. G., Proteins Associated with Thyroid Hormones, *Physiol. Rev.*, 40, 415, 1960. Thus, the measurement of total circulating thyroxine concentration and of thyroxine binding globulin concentration provides a good assessment of the relative concentration of free thyroxine.

Three different methods have been used to assess the level of thyroxine binding globulin concentrations. The oldest method is the T-3 uptake study which measures unsaturated thyroxine binding globulin capacity: *J. Clin. Endocrinol.*, 17:33, January, 1957 and *J. Clin. Endocrin.*, 25:39–54, 1965. T-3 uptake assays use $^{125}I$ labeled liothyronine (T-3) to competitively bind to the free TBG sites and a secondary solid support (viz: resin, charcoal, etc.). After an incubation period and suitable separation technique (Viz: washing, centrifugation, etc.) the remaining radio-activity on the solid support is counted. This radioactivity is inversely proportional to the unsaturated thyroxine binding globulin concentration.

Another methodology is a radioimmunoassay which utilizes antibody specific for thyroxine binding globulin. This methodology does not measure the binding ability of the thyroxine binding globulins: *Clin. Chem. Acta.*, 87, (1978), 373–381.

Another methodology assesses the total thyroxine binding globulin capacity by equilibrating with a large excess of thyroxine to displace the endogenous thyroxine in the sample: U.S. Pat. No. 3,960,492, (1976).

The present invention is a method for determining unsaturated thyroxine binding globulin in serum which has the particular advantage that the determination of unbound tracer, i.e., the thyroxine irreversible enzyme inhibitor conjugate, is sufficiently fast and irreversible so that thyroxine and TBG equilibrium is not disturbed.

BRIEF DESCRIPTION OF THE INVENTION

This invention utilizes reagents having a thyroxine derivative conjugated to an irreversible enzyme inhibitor. That is, an enzyme inhibitor which inactivates the enzyme by forming covalent bonds. The thyroxine irreversible enzyme inhibitor conjugate binds by way of the thyroxine moiety to a site of unsaturation on the thyroxine binding globulin. This binding to the thyroxine binding globulin inactivates the irreversible enzyme inhibitor moiety. Thus, the greater the amount of unsaturated thyroxine binding globulin, the more conjugate that will be bound and the amount of irreversible enzyme inhibitor which will be available to inhibit the enzyme will be reduced. That is: increased amounts of thyroxine binding globulin will result in greater enzyme activity.

Thus, intermixing enzyme and substrate to the enzyme and the above-described thyroxine irreversible enzyme inhibitor with serum permits determination of unsaturated thyroxine binding globulin in serum.

The measurement of unsaturated thyroxine binding globulin is used in conjunction with total thyroxine concentration to determine a free thyroxine index which is a generally accepted marker for the initial assessment of thyroid dysfunction.

DETAILED DESCRIPTION OF THE INVENTION

Representative enzymes and irreversible enzyme inhibitors useful for practicing the present invention are listed in Table I.

TABLE I

| Irreversible Inhibitor | Enzymes |
| --- | --- |
| Organophosphate triesters | Trypsin |
| Organophosphonate diesters | Acetylcholinesterase |
| Organophosphothioates | Butyrlcholinesterase |
|  | Chymotrypsin |
|  | Thrombin |
|  | Elastase |
|  | Adenosine Deaminase |
| Alkylsulfonates | Acetylcholinesterase |
| Alkyl Isocyanates | Elastase |
|  | Trypsin |
|  | Chymotrypsin |
| p-Chloromercuribenzoate Derivatives | Papain |
|  | Alcohol Dehydrogenase |
|  | Chymopapain |
|  | Clostridiopeptidase B |
|  | Adenosine Deaminase |
|  | Lipase |
|  | β-amalyase |
|  | Pepsin |
|  | Glyceraldehyde-3-phosphate Deh. |
| p-Chloromercuribenzoate Derivatives(Continued) | Luciferase |
|  | Aspartate Aminotransferase |
|  | Alanine Aminotransferase |
|  | Hexokinase |
| Substrate Epoxides | Pepsin |
| 6-diazo-5-oxo-L-norleucine Derivatives | Glutaminase A |
| Iodoacetic Acid Derivatives | Acid deoxyribonuclease II |
|  | Alcohol dehydrogenase |
| N-Bromosuccinimide Derivatives | Acid deoxyribonuclease II |
|  | Dextranase |

Organophosphorous irreversible enzyme inhibitors are preferred. J. Am. Chem. Soc., 80, 456, (1958); J. Am. Chem. Soc.; 82, 596, (1960) and Rec. Trav. Chim., 86, 399, (1967) describe several classes of organophosphorous compounds which are suitable irreversible enzyme inhibitors. Preferred organophosphorous compounds useful for conjugation to thyroxine analogs are represented by the following formula:

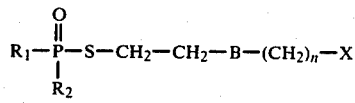

wherein B represents nitrogen or sulfur or their alkylated salts; n is 1–10, preferably 2–8; X represents a functional group such as hydroxy, amino, carboxy, α-halomethylcarboxy wherein the halo is iodo, chloro, or bromo: $R_1$ and $R_2$ represent an alkyl radical having 1–10 carbon atoms or alkoxy having 1-10 carbon atoms. The alkyl radical may be substituted with nitro, halo, cyano, benzyl or similar substituents. Those skilled in the organic chemistry will recognize a wide variety of equivalent structures for practicing the present invention.

Irreversible enzyme inhibitors are bound to thyroxine analogs by conventional bifunctional bridging groups having the general formula:

X—A—Y wherein X and Y represent functional groups such as —OH, —NH$_2$, CO$_2$H (esters), —CO—CH$_2$A, wherein Z is (I, Cl, Br). A represents —(CH$_2$)$_n$— wherein n is 3-20. The alkylene chain may be interrupted with one or more bivalent groups such as —O—, —CO—, —S—, —NH—, —CONH—, —CH=CH—, —C≡C—, phenylene and sulfonium and ammonium salts. The alkylene chain may be substituted with common substituents such as halo (I, Br, Cl, F), hydroxy, cyano, phenyl, amino, carboxy, organo carboxyesters, alkyl having 1-7 carbon atoms, alkoxy having 1-3 carbon atoms. X—A—Y may be a small polypeptide or polysaccharide chain. Thus, X—A—Y is reacted by conventional techniques with an irreversible enzyme inhibitor and thyroxine analog to form amide, ester, amine, imine, sulfonamide, thioester, phosphate, thiophosphate and the like linkages between the bridging group and the irreversible enzyme inhibitor and thyroxine analog.

Most generally, a side chain is built on a thyroxine analog and the product reacted with an irreversible enzyme inhibitor suitably functionalized for reaction with the side chain on the thyroxine analog. Alternatively, a side chain is built on the irreversible enzyme inhibitor and reacted with a suitable thyroxine analog. Thus, compounds of the formula irreversible enzyme inhibitor —A— thyroxine analog are suitable reagents.

The following structures illustrate preferred conjugates for use in conjunction with acetylcholinesterase (E.C. 3.1.1.7):

The reaction involved in the assay for unsaturated thyroxine binding globulin (TBG) are shown as follows:

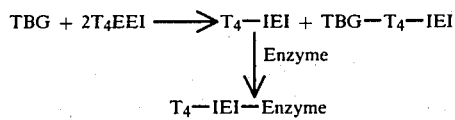

T$_4$IEI represents the thyroxine irreversible enzyme inhibitor conjugate.

T$_4$-IEI-Enzyme represents the conjugate irreversibly bound to an enzyme, the enzyme being inactivated.

TBG-T$_4$-IEI represents thyroxine binding globulin bound to the thyroxine irreversible enzyme inhibitor conjugate thereby inactivating the inhibitor. Thus, the larger the amount of T$_4$-IEI bound to thyroxine binding globulin to form TBG-T$_4$-IEI, the lower the amount of enzyme inhibition. The enzyme-substrate reaction is generally designed to be a colorimetric assay.

A preferred assay uses acetylcholinesterase as in enzyme, acetyl-β-methylthio-choline as a substrate and 5,5'-dithiobis(2-nitrobenzoic acid) as a colorimetric indicator to measure thiocholine liberated from the substrate by the enzyme.

This reaction is monitored at 412 nm. Standards are used to prepare a standard curve from which unknowns are determined.

Colorimetric enzyme analysis are conveniently carried out on a bichromatic spectrophotometer described in U.S. Pat. Nos. 3,748,044; 3,831,618; 3,833,304; 3,900,289; 3,817,425; and 3,811,780.

In a preferred procedure the following three reagents are used:

(A) Diluent Solution 0.1 Molar Sodium barbital
0.1 Molar Magnesium chloride
$6 \times 10^{-3}$ Molar N-methyl orphenadrine sulfate

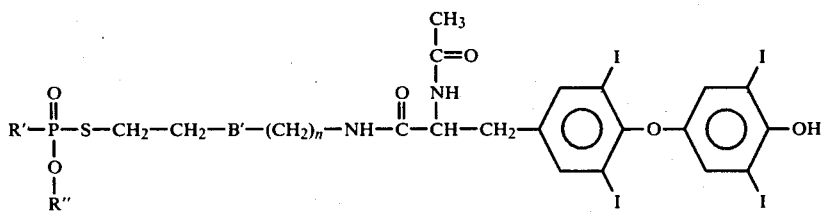

wherein n is 2-8 and R' and R" are alkyl having 1-10 carbon atoms, and B' is —S or the methyl or ethyl sulfonium salt thereof.

CH$_3$—OSO$_3$— or FSO$_3$— salts are particularly suitable for practicing this invention. A compound of the formula is a particularly preferred reagent.

$1.5 \times 10^{-4}$ Molar 5,5' Dithiobis (2-nitrobenzoic acid)
0.1% Bovine serum albumin
0.1% Gelatin
1% Cycloheptaamylose
0.01% Sodium azide

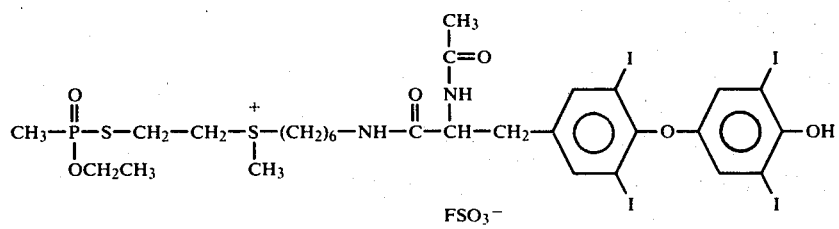

(B) Thyroxine Conjugate with 5,5 Dithiobis(2-nitrobenzoic acid)

$5 \times 10^{-3}$ Molar Sodium citrate
$7 \times 10^{-4}$ Molar 5,5' Dithiobis(2-nitrobenzoic acid)
0.15 Molar Sodium chloride
1% Dextran
$2 \times 10^{-3}$ Molar Acetyl-$\beta$-methylthio-choline iodide
0.1% Gelatin
$7 \times 10^{-9}$ Molar Thyroxine-phosphonate conjugate (C) Enzyme Reagent 6 I.U. Acetylcholinesterase
$1 \times 10^{-2}$ Molar Potassium phosphate
0.1% Dextran
0.01% Sodium Azide
$7.6 \times 10^{-2}$ Molar Sodium Chloride
0.15% Bovine Serum Albumin
0.15% Magnesium Chloride 6 hydrate 100 parts by volume of reagent C is mixed with 1 part by volume of reagent A to form a working reagent. 10 microliters of serum is mixed with 250 microliters of working reagent and 150 microliters of reagent B. The mixture is incubated at 37° C. and monitored by a bichromatic spectrophotometer at 415 nm/550 nm at 5, 10 and 15 minutes (a ABA-100 or VP bichromatic spectrophotometer sold by Abbott Laboratories, Dallas, Texas is suitable). Typical values for water, reference control, and a series of unknown are:

|  |  | Uptake Values |
|---|---|---|
| Ad H₂O | = 0.200 | 0 |
| Ad reference control | = 0.400 | 1.09 |
| Ad Unknown (a) | = 0.500 | 1.64 |
| Ad Unknown (b) | = 0.300 | 0.545 |
| Ad Unknown (c) | = 0.600 | 2.18 |

EXAMPLE 1

Preparation of Thyroxine-Phosphonate Conjugate

To a solution of 5 g of 6-aminohexanol in 50 ml of methylene chloride at 0° C. is added dropwise 9.3 g of di-t-butyldicarbonate. The solution is allowed to come to room temperature and is stirred for 17 hours. The solution is washed with aqueous citric acid, aqueous sodium bicarbonate, and dried over anhydrous magnesium sulfate. The magnesium sulfate is filtered and the solvent evaporated to provide a yellow oil. The oil is purified on silica gel using 3% methanol in methylene chloride as eluent to provide N-t-butoxycarbonyl-6-aminohexanol having the following structural formula:

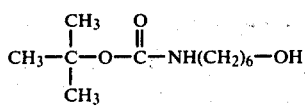

To 5.9 g of this compound and 3.06 g of triethylamine in 50 ml of methylene chloride is added 3.47 g of methanesulfonyl chloride. The solution is stirred for thirty minutes and washed with aqueous citric acid, aqueous sodium bicarbonate, and then dried over anhydrous magnesium sulfate. The magnesium sulfate is filtered and the solvent removed by evaporation to provide N-t-butoxycarbonyl-6-aminohexyl methanesulfonate. In 10 ml of dimethylformamide, without further purification, 6.2 g of this material is added to a solution of 2.5 g of $\beta$-mercaptoethanol in 60 ml of anhydrous dimethylformamide containing 3.5 g of potassium t-butoxide. The mixture is stirred for 17 hours at room temperature. The reaction mixture is poured into water and extracted with methylene chloride. The organic extract is washed with 100 ml of water three times and dried over anhydrous magnesium sulfate. The magnesium sulfate is filtered and the solvent is removed by evaporation. The residual oil is purified by silica gel chromatography using 5% methanol in methylene chloride as eluent to provide N-t-butoxycarbonyl-9-amino-3-thia-1-nonanon, having the formula:

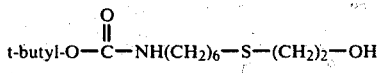

A solution of 2 g of this material and 1.4 g of di-isopropylethylamine in 20 ml of methylene chloride is cooled to 0° C. and 1.64 g of methanesulfonic anhydride is added. After 30 minutes, 1.86 g of di-isopropylethylamine and 2.0 g of O-ethyl methylphosphonothioic acid are added while keeping the reaction mixture at 0° C. The solution is allowed to come to room temperature over 30 minutes and then is refluxed for 2.5 hours. After cooling the product in methylene chloride, it is washed with aqueous sodium bicarbonate and dried over anhydrous magnesium sulfate. The magnesium sulfate is filtered and the solvent is removed by evaporation under reduced pressure. The crude product is purified by column chromatography using 1% methanol in methylene chloride as eluent to provide O-ethyl-S-(N-t-butoxycarbonyl-9-amino-3-thianonyl)methylphosphonothioate, having the following structural formula:

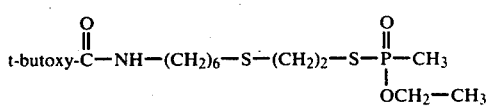

This compound, 250 mg, is stirred in a 2:1 mixture of methylene chloride and trifluoroacetic acid for one hour at room temperature. The solvent is removed by evaporation under reduced pressure. The resulting salt is dissolved in 6 ml of dioxane and 320 mg of diisopropylethylamine is added. Then 620 mg of the N-hydroxysuccinimide ester of N-acetyl-L-thyroxine is added and the mixture is stirred for 16 hours. The reaction mixture is poured into 50 ml of methylene chloride and washed successively with aqueous citric acid and aqueous sodium bicarbonate. The solution is dried over anhydrous magnesium sulfate. The magnesium sulfate is removed by filtration and the solvent is removed by evaporation under reduced pressure. The residual oil is chromatographed on silica gel using 1% methanol in methylene chloride as eluent. Recrystallization from acetonitrile provides 9-(ethoxymethylphosphinylthio)-7-thianonyl-N-acetyl thyroxine amide, having the following structural formula:

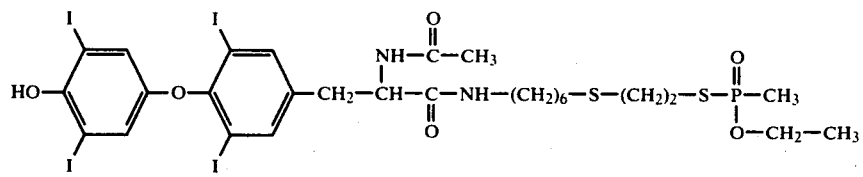

To a solution of 50 mg of this compound in 1.5 ml of methylene chloride is added 10.7 mg of methyl fluorosulfonate. A solid is formed over 2.5 hours. The solvent is decanted and the precipitate is triturated with anhydrous ether to provide a powder, which is the sulfonium salt of the formula:

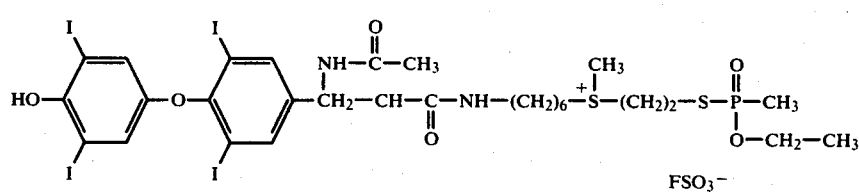

EXAMPLE 2

Following the above procedure of Example 1, replacing 6-aminohexanol with 4-aminobutanol; 5-amino-3-thiapentanol; N-glycyl-6-amino-1-hexanol, respectively, provides:

N-t-butoxycarbonyl-4-amino-1-butanol $$\text{t-butyl-O}-\overset{\overset{O}{\|}}{C}-NH-(CH_2)_4-OH;$$

N-t-butoxycarbonyl-5-amino-3-thia-1-pentanol

-continued $$\text{t-butyl-O}-\overset{\overset{O}{\|}}{C}-NH-(CH_2)_2-S-(CH_2)_2-OH;\text{ and}$$

N[N'-t-butoxycarbonyl)-glycyl]-6-amino-1-hexanol

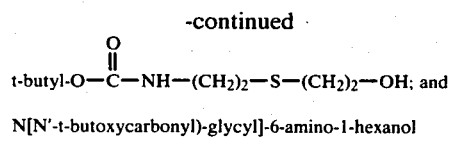

and these alcohols are in turn reacted with methanesulfonyl chloride, β-mercaptoethanol, methanesulfonic anhydride, and O-ethyl methylphosphonothioic acid, where appropriate, to provide inhibitor arms for coupling of the formula:

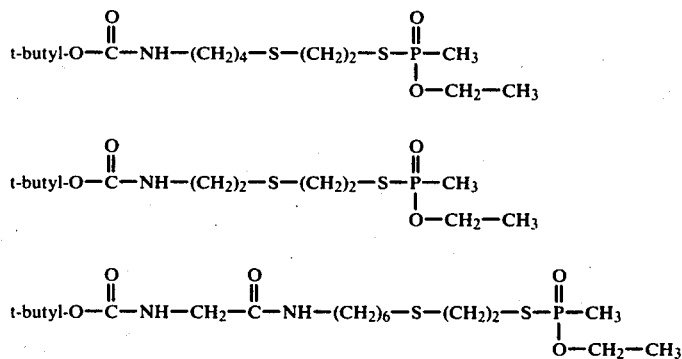

Alternately, O-butyl methylphosphonothioic acid is used to provide compounds such as:

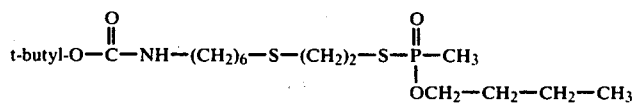

These intermediate reagents are deblocked and then reacted with the N-hydroxysuccinimide ester of N-acetyl-L-thyroxine to provide conjugates such as N-[12-(ethoxymethylphosphinylthio)-10-thia-3-aza-2-oxododecyl]-N$^\alpha$-acetylthyroxine amide, having the following formula:

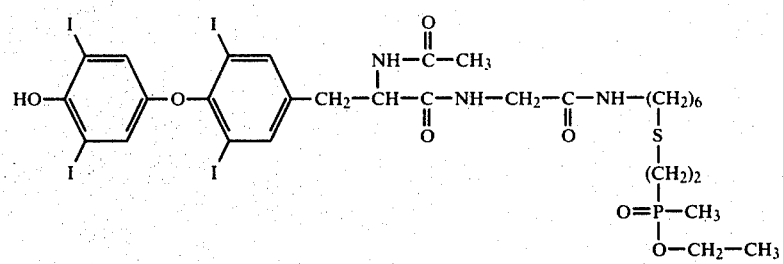

and the corresponding sulfonium salt:

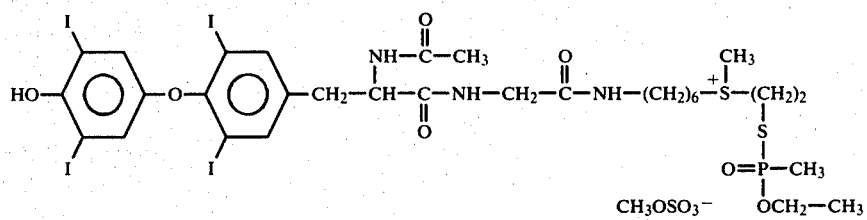

What is claimed is:

1. A method for measuring unsaturated thyroxine binding globulin in serum comprising:
   (a) intermixing with the serum (i) thyroxine irreversible enzyme inhibitor conjugate which binds to the unsaturated thyroxine binding globulin thereby inactivating the irreversible enzyme inhibitor portion of the conjugate (ii) an enzyme which is irreversibly inhibited by the thyroxine irreversible enzyme inhibitor conjugate unbound by the thyroxine binding globulin and (iii) a substrate for the enzyme;
   (b) monitoring the enzyme substrate reaction to obtain test results; and
   (c) comparing test results with a reference.

2. A method according to claim 1 wherein the enzyme is acetylcholinesterase; the thyroxine is conjugated to an organophosphorous irreversible enzyme inhibitor of acetylcholinesterase; and the substrate for acetylcholinesterase is acetyl-$\beta$-methylthio-choline.

3. A method according to claim 1 wherein the enzyme substrate reaction is monitored by measuring $\beta$-methylthio-choline released by acetylcholinesterase utilizing 5,5' dithiobis(2-nitrobenzoic acid) as chromogenic reagent.

4. A method according to claim 2 wherein the conjugate has the formula:

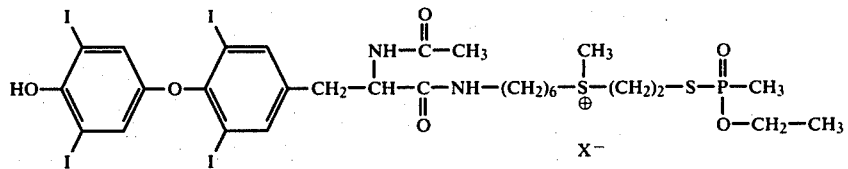

wherein X is $FSO_3^-$ or $CH_3$—$OSO_3^-$.

* * * * *